US011420018B2

(12) United States Patent
Schmit et al.

(10) Patent No.: US 11,420,018 B2
(45) Date of Patent: Aug. 23, 2022

(54) CATHETER-BASED USER INTERFACE DEVICE FOR REMOTE CONTROL OF DISPLAY IMAGES

(71) Applicant: General Electric Company, Schenectady, NY (US)

(72) Inventors: Rodger F. Schmit, Wauwatosa, WI (US); Adrian F. Warner, Wauwatosa, WI (US); Daniel R. Schneidewend, Wauwatosa, WI (US); Timothy P. Stiemke, Wauwatosa, WI (US)

(73) Assignee: General Electric Company, Schenectady, NY (US)

(*) Notice: Subject to any disclaimer, the term of this patent is extended or adjusted under 35 U.S.C. 154(b) by 478 days.

(21) Appl. No.: 16/445,881

(22) Filed: Jun. 19, 2019

(65) Prior Publication Data

US 2019/0298970 A1  Oct. 3, 2019

Related U.S. Application Data

(62) Division of application No. 15/218,611, filed on Jul. 25, 2016, now abandoned.

(51) Int. Cl.
*A61B 5/00* (2006.01)
*A61M 25/01* (2006.01)
*A61B 34/20* (2016.01)
*A61B 17/00* (2006.01)

(52) U.S. Cl.
CPC ......... *A61M 25/0113* (2013.01); *A61B 34/20* (2016.02); *A61B 5/6852* (2013.01); *A61B 2017/00199* (2013.01); *A61B 2017/00212* (2013.01); *A61B 2017/00221* (2013.01); *A61B 2017/00734* (2013.01)

(58) Field of Classification Search
None
See application file for complete search history.

(56) References Cited

U.S. PATENT DOCUMENTS

| 85,314,281 | 9/2013 | Glynn et al. |
| 9,000,720 B2 | 4/2015 | Stulen et al. |
| 2003/0069719 A1 | 4/2003 | Cunningham et al. |

(Continued)

FOREIGN PATENT DOCUMENTS

| WO | 2007024983 | 3/2007 |
| WO | 2011123669 | 10/2011 |
| WO | 2013101269 | 7/2013 |

*Primary Examiner* — Joel F Brutus
(74) *Attorney, Agent, or Firm* — Boyle Fredrickson, SC

(57) ABSTRACT

In the present invention, an interface control module for controlling a mapping/imaging/recording system is provided for placement on a catheter control handle. The interface control module includes control elements that are operably connected to the mapping/imaging/recording system in order to control various functions of the imaging/recording system relating to images represented on a display forming a part of the mapping/imaging/recording system. The interface control module can be integrated with the catheter control handle or can be formed as a separate component that is releasably attachable to the catheter control handle to enable a use to operate the mapping/imaging/recording system from the catheter control handle being utilized in an interventional medical procedure.

13 Claims, 3 Drawing Sheets

(56) References Cited

U.S. PATENT DOCUMENTS

2007/0083193 A1* 4/2007 Werneth .............. A61B 5/7435
606/41
2013/0165854 A1 6/2013 Sandhu et al.

* cited by examiner

CATHETER-BASED USER INTERFACE DEVICE FOR REMOTE CONTROL OF DISPLAY IMAGES

CROSS-REFERENCE TO RELATED APPLICATION

This application is a divisional of U.S. application Ser. No. 15/218,611, filed Jul. 25, 2016, the entirety of which is incorporated herein.

BACKGROUND OF INVENTION

The invention relates generally to catheter controls, and more particularly to a control system for an imaging/recording system designed to be disposed on an existing catheter control device for remote control of images that are presented on a remote display.

Catheters are used in an increasing number of medical procedures to evaluate various conditions of the patient with which the catheter is utilized. In performing the procedure with the catheter, with most catheter designs the physician must hold the handle for the catheter with one hand while operating the controls on the handle with the other hand to move the catheter tip into the desired location to obtain images of the tissue being investigated and/or treated. However, as the controls for the operation of the imaging/recording system are separate from the catheter, if the physician wishes to control the imaging/recording system connected to the catheter to alter or change the display of the images provided by the catheter tip or to activate the display in order to take a measurement of a structure being illustrated on the display, the physician must choose to take a hand off of the handle or catheter controls in order to adjust/operate the image display, which is undesirable.

As an alternative to having the physician remove their hand from the catheter handle, certain prior art solutions have been developed. In particular, one prior art solution involves another person who is utilized to perform an action regarding the operation of the imaging/recording system as requested by the physician. Specifically, as the lab/operating room and the control system computer are very often in different rooms, a head set is used by the physician to communicate with the recording technician who is actually making the measurement by operating the imaging/recording system/display controls. As another prior art solution to the problem, a physician will have another individual perform the manipulation of the catheter, while the physician is in the control room operating the imaging/recording system display controls to make the actual measurement as desired.

When there are staff shortages or transitions of the individuals between locations, this utilization of the separate individual can delay or unduly complicate a procedure. In addition, physicians generally prefer to these associated functions themselves such that the addition of another person can cause undue stress on the physician.

Other prior art solutions to this issue have included the substitution of a robot for the physician in the lab or operating room such that the physician can control the robot, which moves the catheter, and the imaging computer. However, similar to the use of the separate individual, the use of a robot removes the physician from the lab or operating room, lessening the ability of the physician to use his or her experience in performing the procedure. The use of a robot also introduces a significant level of increased complexity to the procedure, as well as the associated increased cost.

Still other prior art solutions include devices separate from the catheter that are positioned around the operating or patient-support table for control of the imaging/recording system functions, such as a foot pedal disposed adjacent the operating table. However this type of solution still requires the physician to shift focus off of the catheter handle in order to operate the control.

Still other alternative prior art solutions that have been proposed include voice control or eye control of the display. However, in either case, the solution presents difficulties when fine motor skill manipulation is required for the operation of the display controls.

Accordingly, it is desirable to develop a system and method for the control of a imaging system and associated display by a user/physician in a lab or operating room that enables the physician to initiate certain related and specific system functions with minimal hand movement, while observing a local display monitor without additional interaction of either recording staff, or support staff in the lab.

BRIEF DESCRIPTION OF THE INVENTION

There is a need or desire for an imaging, mapping and/or recording system including a user interface control disposed directly on the catheter handle that enables the user to operate a catheter while also initiating certain related and specific system functions of the imaging/recording system. The mapping/imaging/recording system control can be operated by the user/physician using the interface control with minimal hand movement while simultaneously securely holding the catheter handle and observing the images displayed by the mapping/imaging recording system on a local display monitor. The above-mentioned drawbacks and needs are addressed by the embodiments described herein in the following description.

According to one exemplary non-limiting aspect of the invention, a handle for a catheter is provided that includes controls for the manipulation of the catheter and that also incorporates a user interface control for the targeted control of very specific functionality of the mapping/imaging/recording system for the physician in the interventional lab/operating room. The physician working at an operating/patient-support table in an interventional lab/operating room uses imaging and signal recording equipment extensively to perform the clinical procedure in conjunction with the catheter. As the prior art interaction methods with the imaging and recording equipment/systems available to the physician can be challenging when simultaneously probing and maintaining complex positions with the catheter relative to the patient's anatomy, the user interface control positioned on the catheter handle allows the physician to remain in control of the catheter handle while also controlling the functions of the imaging/recording system as required. The user interface control on the handle includes separate control features to be used by the physician in operating the imaging system to control the imaging/recording system such as to control the image being shown on an associated monitor and/or to take measurements of various structures illustrated on the displayed images.

According to another aspect of one exemplary non-limiting embodiment of the invention, a catheter control handle includes a housing, a shaft extending outwardly from the housing, a conductor extending outwardly from the housing and configured to be connected to an mapping/imaging/recording system to supply image data thereto, a control device disposed on the housing and connected to the shaft to control the shaft and an interface control module disposed on the housing, the interface control module configured to be connected to the imaging/recording system to control the operation of the imaging/recording system.

According to still a further aspect of one exemplary non-limiting embodiment of the invention, a mapping/imaging/recording system interface control module for a catheter control handle includes a housing configured to be secured to a control handle and a number of control elements disposed on the housing, wherein the control elements are operably connected to the mapping/imaging/recording system to control the operation of different functions of the mapping/imaging/recording system.

According to still a further aspect of one exemplary non-limiting embodiment of the invention, a method of controlling a mapping/imaging/recording system from a catheter control handle during an interventional medical procedure includes the steps of providing a catheter control handle including a housing, a shaft extending outwardly from the housing, a conductor extending outwardly from the housing and connected to an imaging/recording system to supply image data thereto, a control device disposed on the housing and connected to the shaft to control the shaft and an interface control module disposed on the housing, the interface control module connected to the mapping/imaging/recording system to control the operation of the mapping/imaging/recording system, operating the interface control module to select an operational function of the imaging/recording system and operating the interface control module to control the operational function of the mapping/imaging/recording system.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
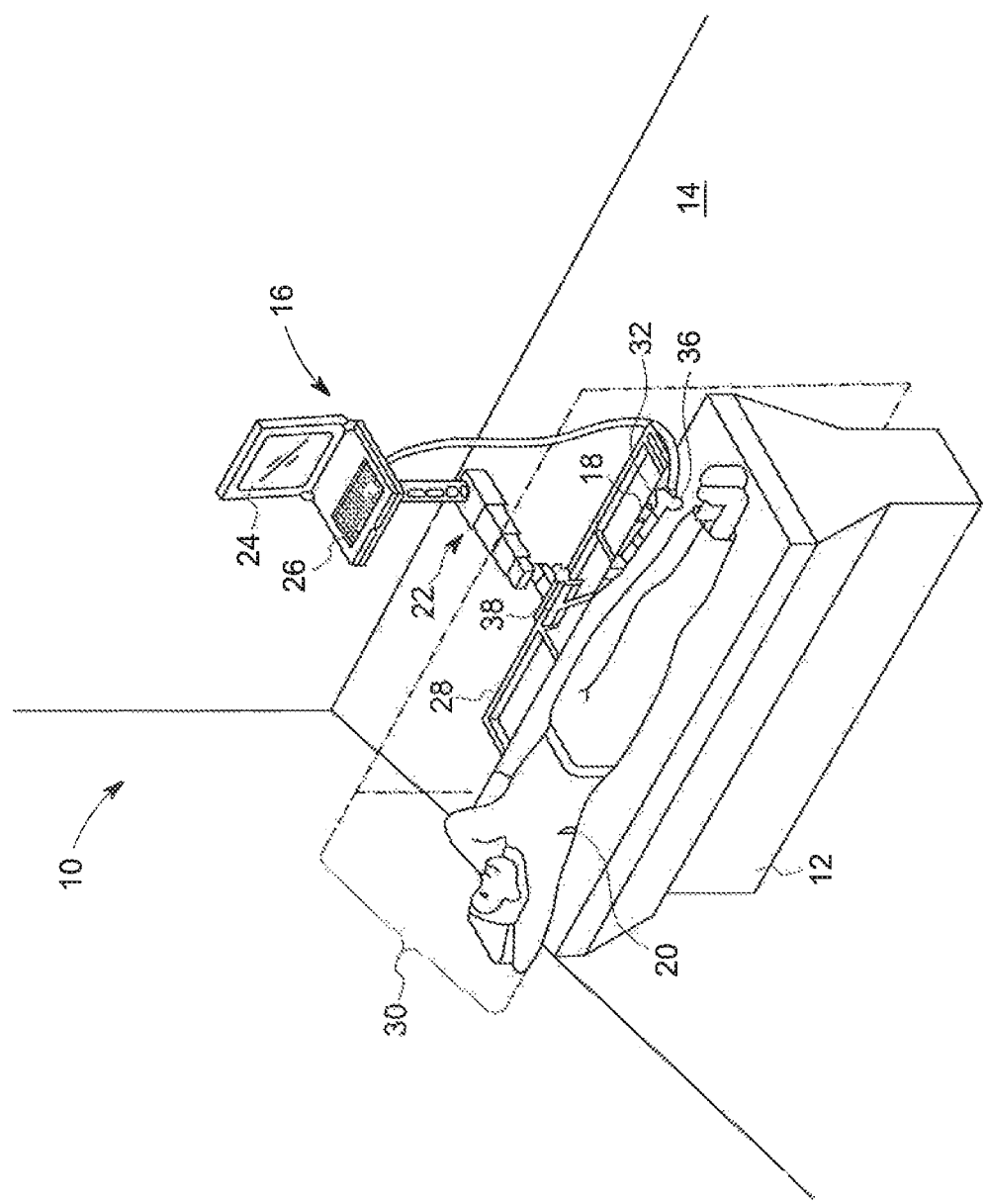
FIG. 1 is a schematic representation of an imaging, mapping and/or recording system including a catheter control handle according to one exemplary non-limiting embodiment of the present invention.

Referring to FIG. 1, in the illustrated exemplary non-limiting embodiment a patient care facility 10, such as an interventional lab/operating room 14, includes a patient bed 12, a medical mapping, imaging and/or recording device or system 16, and a catheter 18. Patient bed 12 is configured to support a patient 20 in the interventional lab/operating room 14 so that medical mapping/imaging/recording device or system 16 may obtain internal medical images of patient 20 using the catheter 18. In various exemplary non-limiting embodiments, patient bed 12 may be a bed of any suitable design that is capable of supporting the patient 20 while performing the imaging procedure with the system 16 and the catheter 18.

The medical mapping/imaging/recording device or system 16 can be any suitable device for obtaining, mapping, recording and/or manipulating images of the selected tissue within the patient 20 via the catheter 18, such as the system disclosed in US Patent Application Publication No. US2005/0209524A1, entitled System And Method For Receiving And Storing Information Pertaining To A Patient, which is expressly incorporated herein by reference in its entirety for all purposes. In the illustrated exemplary non-limiting embodiment of FIG. 1 the system 16 may include a mounting structure 22 connected to the table 12 that supports a display screen 24 on which the physician can view the images provided by the catheter 18. The system 16 can also include an interface 26 operably connected to the display 24 and which can be utilized by a physician operate the system 16 to illustrate selected images on the display and/or to obtain measurements on the images illustrated on the display 24. The imaging/recording system 16 can additionally be configured to be operably connected in a known manner, such as by using a wired or wireless connection, to a computer network (not shown) located within the patient care facility 10 in order to transmit the data and images obtained by the system 16 to and via the network to a remote location, as desired.

In the illustrated exemplary non-limiting embodiment, the mounting structure 22 is configured to support imaging device 16 and is coupled to bed 12 via a rail 28 in an area external to a sterile zone or field 30 encompassing bed 12. In another exemplary non-limiting embodiment, mounting structure 22 may be coupled to bed 12 via means other than a rail. Mounting structure 22 is capable of positioning device 16 in a variety of locations as desired by a clinician for various reasons such as for best viewing or so as to not be obstructing any procedure performed on patient 20. In other exemplary non-limiting embodiments, mounting structure 22 may be a cart that is not directly coupled to bed 12.

Catheter 18 can be any suitable type of catheter utilized to perform an interventional procedure on the patient 20, and is configured to be inserted into patient 20 to cooperate with device/system 16 and obtain medical imaging data for representation on the display 24. In the exemplary non-limiting illustrated embodiment of FIG. 2, the catheter 18 includes a control handle 36 through which extends a shaft for insertion into the patient 20. The handle 36 is operatively connected opposite the shaft 32 to a conductor 34 that connects the handle 32 to the imaging/recording system 36 and extends through shaft. The conductor 34 enables the image signals obtained by the shaft 32 to be transmitted along the conductor 34 though the catheter 18 to the system 16 for display and manipulation by the system 16.

The control handle 36 includes a housing 37 configured to allow gripping of die catheter 18 by a user. The control handle 36 may be manipulated by a user/physician to guide the shaft 32 to a desired location within the patient 20 to obtain and retrieve data from within patient 20, such as imaging data for use by the system 16. In one exemplary non-limiting embodiment, the control handle 36 includes a control device 40 that enables the user/physician to operate the shaft 32 within the patient 20 to move the shaft 32 into the desired positions within the patient 20 to obtain the desired image data. The control device 40 can have any suitable or desired configuration to enable the physician to remotely manipulate the position of the shaft 32 within the patient 20 as desired.

The control handle 36 additionally includes a user interface control module 42 disposed thereon. The interface control 42 is operatively connected to the mapping/imaging/recording system 16, such as via the conductor 34 or another suitable wired or wireless connection, in order to provide the user/physician with controls on the control handle 36 for the direct operation of the various functions of the mapping/imaging/recording system 16. In the illustrated exemplary non-limiting embodiment of FIG. 2, the interface control 42 includes a number of control elements 43, such as buttons 44,45 that can be configured to activate and deactivate the interface control 42 and to select the functions of the mapping/imaging/recording system 16 to be controlled. The control elements 43 can also include a rotatable knob or thumb wheel 46 disposed adjacent the buttons 44,45 that is operable to move the user/physician through the various functions of the system 16 to reach the desired function for selection using one of the buttons 44,45. In one exemplary non-limiting embodiment, the thumb wheel 46 is used to move a display element (not shown) that is represented on the display 24 in a horizontal or vertical direction to enable the physician to indicate or highlight which function of the system 16 is to be accessed. Once the desired function is highlighted, the user can operate the button 44 to select the desired function to be controlled. After selection, the physician can utilize one or more of the buttons 45 and/or the thumb wheel 46 to control the selected function of the system 16. In doing so, the physician does not have to remove a hand from the handle 36, as the buttons 44,45 and wheel 46 for the interface control 42 are disposed directly on the handle 36 adjacent the control device 40 for the shaft 32.

Figure 2:
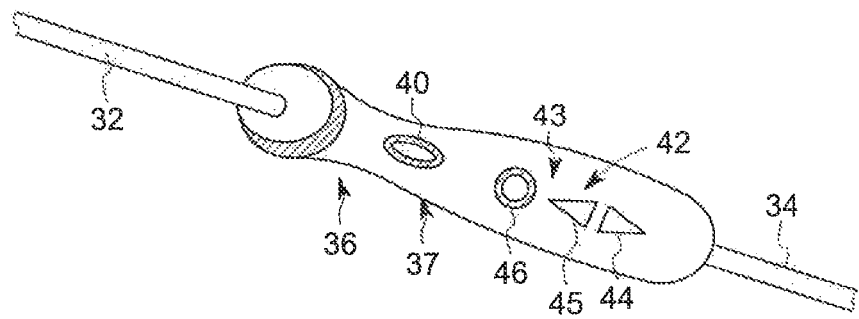
FIG. 2 is an isometric view of a control handle including an interface control for the imaging mapping and/or recording system of FIG. 1 according to an exemplary non-limiting embodiment of the invention.
Figure 3:
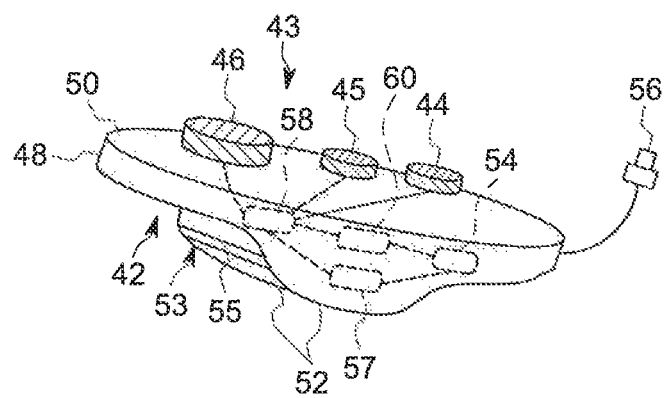
FIG. 3 is an isometric view of the interface control module according to another exemplary non-limiting embodiment of the invention.
Figure 4:
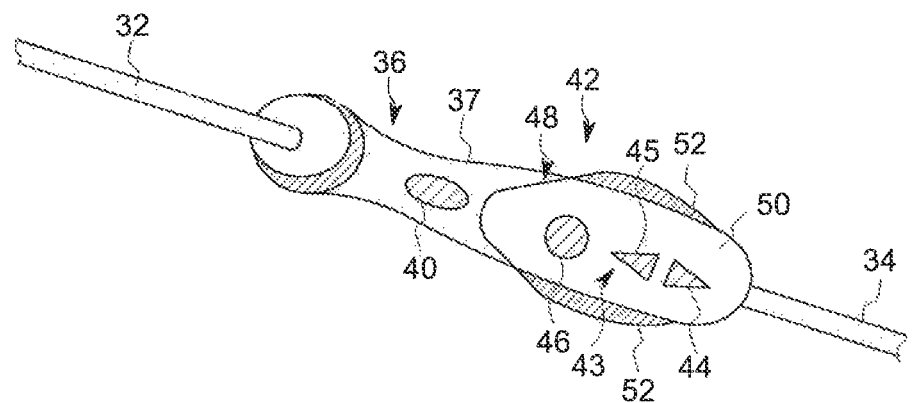
FIG. 4 is an isometric view of the interface control module of FIG. 3 secured to a catheter control handle according to another exemplary non-limiting embodiment of the invention

In the illustrated exemplary non-limiting embodiment of FIG. 2, the interface control module 42 is integrated directly into the housing 37 of the control handle 36 to provide a seamless physical integration of the interface control 42 with the handle 36. In an alternative exemplary non-limiting embodiment illustrated in FIGS. 3 and 4, the interface control 42 can include a housing 48 that is separate from the housing 37 of the control handle 36. The housing 48 is formed of any suitable material, such as of a material that is the same as or similar to that used to form the control handle 36, and includes the control buttons 44,45 and wheel 46 thereon. The housing 48 has an upper portion 50 on which the buttons 44,45 and wheel 46 are disposed that conforms to the shape of the control handle 36. A pair of lower portions 52 extend downwardly from the upper portion on opposite sides of the upper portion 50 and are configured to engage and hold the housing 48 on the control handle 36 in a secure and stable manner. To accomplish this, the lower portions 52 include an engagement structure 53 thereon, such as a rib 55 that is releasably engageable within a complementary groove (not shown) formed in the catheter control handle 36, that operates to engage the housing 48 with the control handle 36 in a suitable and releasable manner, such as by frictionally engaging the control handle 36.

As the housing 48 is not directly connected to the conductor 34 within the control handle 36 as in the prior exemplary non-limiting embodiment, the housing 48 includes a wireless transceiver 54 capable of communicating with the system 16, such as by using near field communications (NFC) technology, Bluetooth® or WiFi signals in order to transmit the control functions initiated by the physician on the housing 48 using the buttons 44,45 and/or wheel 46 to the system 16. In an alternative exemplary non-limiting embodiment, the housing 48 can include a separate, and optionally separable, plug-in cable 56 that extends outwardly from the housing 48 and is connectable within a suitable port (not shown) disposed on the control handle 36 or on the system 16. Further, the housing 48 can include a suitable power source 57 capable of operating the interface control module 42. The power source 57 can be replaceable or rechargeable, or can be omitted entirely with the power supplied to the interface control module 42 coming through the plug-in cable connected to the housing 48. Additionally, the housing 48 may include a processing unit 58 for directing the control signals supplied via the control elements 43 and electronic storage media 60 operably connected to the processing unit capable of storing various information concerning the operation of the interface control module 42. Further, in order to avoid sterility issues with regard to the use of the module 42, the module 42 can be disposable after use.

In another exemplary non-limiting embodiment, where the interface control 42 is formed integrally with the control handle 36 or as a connectable housing 48, the user interface signals generated by the operation of the interface control 42 using the buttons 44,45 and/or the wheel 46 can be modulated with the signal from the conductor 34 such that the interface control signal can be separately decoded at the signal conditioning/amplification module (not shown) within the system 16.

Figure 5:
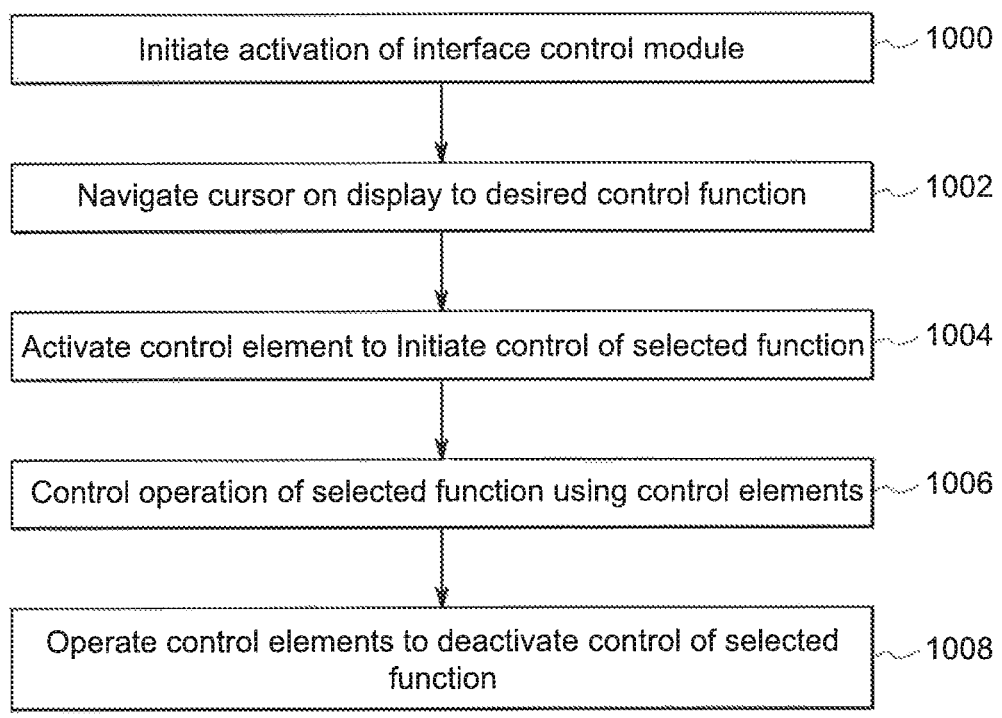
FIG. 5 is a schematic of a method of operation of the interface control module according to an exemplary non-limiting embodiment of the invention.

In one exemplary non-limiting embodiment of a method of operation of the interface control 42, shown in FIG. 5, in block 1000 the operation of the interface control 42 is initiated by the user depressing an activation or power button 44 on the interface control module 42 on the catheter control handle 36. This activation will pull up a display icon or cursor (not shown) on the display 24 for use indicating the function desired to be controlled by the user. The user/physician in block 1002 can then navigate the cursor on the display 24 in the horizontal or vertical plane by operating the button 44, such as by using a second double click, by the use of other buttons 45, or by the use of the thumb wheel or knob 46 to move the cursor onto the icon for the desired control function on the display screen 42. Once on the desired icon, the user in block 1004 can depress button 44 to activate control of the selected function of the system 16. The system function can then be controlled in block 1006 by the operation of the control elements, 43, e.g., the buttons 45 and/or the knob/wheel 46. When the user is finished operating or controlling the system function, in block 1008 the user can depress button 44 again to cease the control of the system function using the interface control module 42.

As an alternative embodiment to the direct navigation of the icon on the display 24 to select the desired system function to be controlled illustrated in FIG. 5, the interface control module 42 can be configured with a number of predetermined sequences, sets or series of clicks or activations of the control elements, e.g., button 44,45 or wheels 46, to automatically initiate very targeted specific system functions, such as pulling up a set of measurement calipers (not shown) on the display 24. In this embodiment, for example, the first click of button 44 can bring up two parallel measurement lines (vertical=amplitude, horizontal=time) on the display 24 over a particular image. A subsequent click of button 44 then initiates the movement of the second parallel line on the display 24, such that a measurement of time or amplitude can be made on the image using the interface control module 42. The measurements taken in this manner are illustrated on the display 24 such that the user/physician can clearly see the measurement on the display 24. This embodiment of the interface control module 42 can also be used to make complex multi-parameter measurements on the display 24 or similar measurements where a measurement point is required to be identified and a marker, or measurement caliper located on the image on the display 24.

With the deployment of the interface control module 42 within or on the control handle 36, the interface control 42 provides the physician with the ability to readily and easily control the function of the imaging/recording system 16 in a manner that allows the physician to maintain control of the catheter 18 during the procedure and to manipulate the images shown on the display 24 directly in the interventional lab/operating room 14 where the physician can immediately utilize the information shown by the system 16 on the display 24 in performing the procedure on the patient 20. Further, other technical advantages of the interface control module 42 include:
- the ability to provide a solution to user interface manipulation at the catheter handle, directly at the physicians hand;
- the ability to enable quick access to dedicated controls without significantly moving the catheter, or removing ones hand from the catheter;
- the ability to deliver functionality to the physician without use of a third party or reliant upon verbal communication; and
- the ability to enable rapid response at the bedside based on the information provided to the physician via the control of the images displayed by the system 16.

In addition to the technical advantages, the commercial advantages of the interface control module 42 include:
- providing a small efficiency improvement to the physician by local imaging system control access;
- not requiring a break in concentration to operate/control the mapping/imaging/recording system 16 using the interface control module 42;
- reducing the dependency on third persons to support certain specific activities such as measurement;
- the integration of the interface control module 42 into a catheter control handle 36, or an add-on device to an existing handle 36;
- the interface control module 42 an be made disposable to minimize sterilization and battery life issues; and
- unique user interaction model support, as a competitive differentiator.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A catheter control handle comprising:
a housing;
a shaft extending outwardly from the housing;
a conductor extending outwardly from the housing and configured to be connected to a mapping imaging/recording system to supply image data thereto;
a control device disposed on the housing and connected to the shaft to control the shaft; and
an interface control module disposed on the housing, the interface control module configured to be connected to the imaging/recording system to control the operation of the mapping/imaging/recording system.

2. The control handle of claim 1 wherein the interface control module comprises a number of control elements disposed on the housing adjacent the control device and configured to be connected to the mapping/imaging/recording system to control the operation of the imaging/recording system.

3. The control handle of claim 2 wherein the number for control elements comprise:
a number of buttons disposed on the housing; and
a number of rotatable knobs disposed on the housing.

4. The control handle of claim 2 wherein the interface control module comprises:
a processing unit operably connected to the control elements; and
electronic storage media operably connected to the processing unit and configured to store sequences of operation of the control elements for automatic control of the mapping/imaging/recording system.

5. The control handle of claim 2 wherein the interface control module is operably connected to the conductor.

6. A method of controlling an imaging/recording system from a catheter control handle during an interventional medical procedure, the method comprising the steps of:
providing a catheter control handle including a housing, a shaft extending outwardly from the housing, a conductor extending outwardly from the housing and connected to a mapping/imaging/recording system to supply image data thereto, a control device disposed on the housing and connected to the shaft to control the shaft and an interface control module disposed on the housing, the interface control module connected to the imaging/recording system to control the operation of the mapping/imaging/recording system;
operating the interface control module to select an operational function of the mapping/imaging/recording system; and
operating the interface control module to control the operational function of the mapping/imaging/recording system.

7. The method of claim 6 further comprising the step of holding the housing of the catheter control handle simultaneously with the step of operating the interface control module to select an operational function of the mapping/imaging/recording system.

8. The method of claim 6 wherein the interface control module comprises a number of control elements, and wherein the step of operating the interface control module to select an operational function of the mapping/imaging/recording system comprises operating the control elements to select an operational function illustrated on a display operably connected to the mapping/imaging/recording system.

9. The method of claim 6 wherein the interface control module comprises a number of control elements, and wherein the step of operating the interface control module to control an operational function of the mapping/imaging/recording system comprises operating the control elements to control an operational function illustrated on a display operably connected to the imaging/recording system.

10. The method of claim 6 further comprising the step of engaging the interface control module with the housing prior to operating the interface control module to select an operational function of the mapping/imaging/recording system.

11. The method of claim 6 further comprising the step of engaging the interface control module with the imaging/recording system prior to operating the interface control module to select an operational function of the mapping/imaging/recording system.

12. The method of claim 11 wherein the step of engaging the interface control module with the imaging/recording system comprises connecting a cable between the interface control module and the mapping/imaging/recording system.

13. The method of claim 11 wherein the step of engaging the interface control module with the mapping/imaging/recording system comprises wirelessly connecting the interface control module and the mapping/imaging/recording system.

* * * * *